United States Patent

Baus et al.

Patent Number: 5,484,938
Date of Patent: Jan. 16, 1996

[54] 1-HYDROXYIMIDAZOLE COMPOUNDS

[75] Inventors: Ulf Baus, Dossenheim; Wolfgang Reuther, Heidelberg-Ziegelhausen, both of Germany

[73] Assignee: BASF Aktiengesellschaft, Ludwigshafen, Germany

[21] Appl. No.: 800,065

[22] Filed: Nov. 27, 1991

Related U.S. Application Data

[62] Division of Ser. No. 586,947, Sep. 24, 1990, Pat. No. 5,112,985.

[30] Foreign Application Priority Data

Sep. 29, 1989 [DE] Germany .................. 39 32 552.0

[51] Int. Cl.$^6$ .................. C07D 233/68; C07D 233/56
[52] U.S. Cl. .................. 548/335.1; 548/343.1
[58] Field of Search .................. 548/337, 335.1, 548/343.1

[56] References Cited

U.S. PATENT DOCUMENTS 3,850,953 11/1974 Mamalis et al. .
4,945,166 7/1990 Baus et al. .

FOREIGN PATENT DOCUMENTS 53-79404 1/1980 Japan .

OTHER PUBLICATIONS

Pachler et al., Journal of Molecular Structure, 76 (1981), 49–64, THEOCHEM, Elsevier Scientific Publishing Co.
Hauser et al, "1–Hydroxyimidazole Derivatives, etc" Sci. Pharm. 56, 235–241 (1988).
Rachler et al, "INDO MO Calculations, etc" J. of Molecular Structure, 76 (1981) 49–64.
Laus et al, "1–hydroxyimidazole derivatives, etc" Synthesis (10), 773–5 (1989).
Hauser et al "1–hydroxyimidazole derivatives, etc" Ca 111:174035r (1989).
Sugijima et al, "Photoresist patterns for, etc" CA 93:59663s.
Pachler et al, "INDO MO Calculations of the, etc" CA 94:174094q (1981).

*Primary Examiner*—Patricia L. Morris
*Attorney, Agent, or Firm*—John H. Shurtleff

[57] ABSTRACT

The preparation of 1-hydroxyimidazoles of the formula I

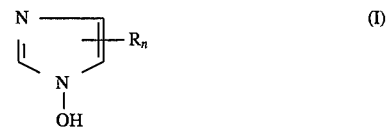

where the R radicals can be identical or different and are each halogen or an organic radical, it also being possible for vicinal radicals to be connected to form an aromatic or nonaromatic ring of from 3 to 12 carbon atoms, and n is from 0 to 3, entails reacting an imidazole of the formula II

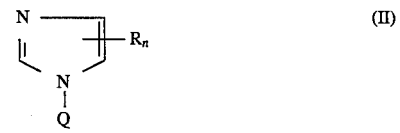

where Q is preferably hydrogen or, especially where R is not halogen, an alkali metal or alkaline earth metal cation, with an organic peroxide.

The 1-hydroxyimidazole and its halogen substituted derivatives of the formula I and the acid addition salts thereof are valuable intermediates for organic syntheses.

4 Claims, No Drawings

1-HYDROXYIMIDAZOLE COMPOUNDS

This application is a division of application Ser. No. 586,947, filed Sep. 24, 1990, now U.S. Pat. No. 5,112,985.

The present invention relates to a novel process for preparing 1-hydroxyimidazoles of the formula I

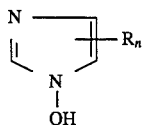

where the R radicals can be identical or different and are each halogen or an organic radical, it also being possible for vicinal radicals to be connected to form an aromatic or non-aromatic ring of from 3 to 12 carbon atoms, and n is from 0 to 3.

DE-A-2 063 857 and DE-A-2 619 381 disclose imidazoles which are substituted in the 1 position and have fungicidal and antimycotic activity.

They are obtained, as is also described in detail in Chem. Ber., 102 (1969) 4177–4187, by cyclization of the correspondingly substituted precursors, e.g. aldehydes, oximes and amines.

However, many 1-hydroxyimidazoles can be obtained only with difficulty, if at all, by these methods, so that it is an object of the present invention to provide a novel process for preparing 1-hydroxyimidazoles, which allows, in particular, the preparation of the hitherto unknown 1-hydroxyimidazole and the halogen derivatives thereof.

We have found that this object is achieved by a novel process for preparing 1-hydroxyimidazoles of the formula I

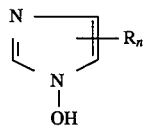

where the R radicals can be identical or different and are each halogen or an organic radical, it also being possible for vicinal radicals to be connected to form an aromatic or nonaromatic ring of from 3 to 12 carbon atoms, and n is from 0 to 3, which comprises reacting imidazoles of the formula II

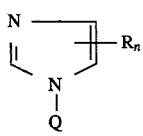

where Q is preferably hydrogen or, especially where R is not halogen, an alkali metal or alkaline earth metal cation, with an organic peroxide.

Compounds where Q is hydrogen are generally preferred. We have also found the novel compounds Ia

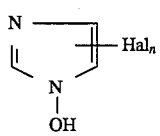

where the halogens (Hal) can be identical or different and n is from 0 to 3, and the acid addition salts of Ia.

In principle, suitable organic peroxides are all compounds of this class, e.g. peracids such as the percarboxylic acids, peracetic acid, perbenzoic acid, m-chloroperbenzoic acid, perpropionic acid, perbutyric acid, permaleic acid, monopersuccinic acid and, in particular, monoperphthalic acid, or persulfonic acids such as p-bromotoluenepersulfonic acid, methanepersulfonic acid and, in particular, toluenepersulfonic acid, and peranhydrides such as diacetyl peroxide, dipropionyl peroxide and, in particular, dibenzoyl peroxide.

The starting material can be either the free imidazole II (Q=H) (variant 1) or its alkali metal or alkaline earth metal imidazolide (Q=alkali metal or alkaline earth metal), which is prepared first and then reacted with the peroxide (variant 2).

The reaction is preferably carried out in a strongly basic medium. Alkali metal and alkaline earth metal hydroxides are used as bases, preferably sodium and potassium hydroxide. These two embodiments are explained in detail hereinafter:

Variant 1:

All starting compounds II can be used in this procedure. Not less than stoichiometric amounts of peroxide are necessary to achieve complete conversion of the imidazole II. However, the molar ratio of peroxide to imidazole II is preferably from 1.5:1 to 5:1, in particular 2:1 to 3:1. It is advisable to carry out the reaction in a solvent or diluent. Suitable for this purpose are all liquids which are essentially inert to peroxides, e.g. water, mixtures of water and acetone, tetrahydrofuran, diethylene glycol dimethyl ether, methylene chloride or chloroform. Since the peroxides are very reactive, the reaction takes place at from 0° to 50° C.

Higher temperatures, say up to 80° C., generally have no advantages. Room temperature is preferably employed.

Variant 2

This embodiment is preferred when the imidazoles II are very costly, and high yields of I are therefore required. However, it is restricted to those imidazoles II which have no halogen in the molecule. On the other hand, active hydrogen atoms, e.g. of hydroxyl groups, do not interfere; on the contrary, correspondingly more of the metalating agent is needed to prepare the imidazolides in this case. Metalating agents with which the free imidazole II (Q=H) is initially reacted are organometallic compounds, e.g. metal alkyls such as n-butyllithium, tert-butyllithium and methyllithium, metal aryls such as phenyllithium, suspensions of alkali metals such as sodium or potassium in toluene, alkali metal hydrides such as lithium hydride, potassium hydride and, in particular, sodium hydride, and alkaline earth metal hydrides such as calcium hydride.

It is advisable, in order to achieve complete conversion, to choose a ratio of imidazole II to salt-forming reagent of from 1:1 to 10:1. Then from 1 to 5 moles of peroxide, based on the imidazole II, are added, where appropriate forming the peroxide in situ from organic compound and hydrogen peroxide.

The reaction is preferably carried out in a solvent. Suitable for this are all inert solvents, e.g. ethers such as diethyl ether, methyl butyl ether, tetrahydrofuran and dioxane, glycol ethers such as diethylene glycol dimethyl ether and triethylene glycol dimethyl ether, aliphatic hydrocarbons such as pentane, hexane, petroleum ether and cyclohexane, aromatic hydrocarbons such as benzene and toluene, and mixtures of these solvents.

Because of the addition of a salt-forming substance, the reaction is preferably carried out at from −20°C. to +50° C., in particular at from 0° C. to +15° C. The solvent is added in an amount of from 5 to 50% by weight.

No special details need be mentioned for either of the methods in the process according to the invention. This also applies to the working up of the reaction mixture.

The process according to the invention is suitable for preparing any desired imidazoles I, where the R radicals preferably have the following meanings:

hydrogen;

alkyl such as $C_1$–$C_{20}$-alkyl, preferably $C_1$–$C_8$-alkyl, particularly preferably $C_1$–$C_4$-alkyl such as methyl, ethyl, n-propyl, isopropyl, n-butyl, isobutyl, sec-butyl and tert-butyl;

halogen such as fluorine, chlorine, bromine and iodine, preferably chlorine, bromine and iodine, particularly preferably chlorine;

aryl such as phenyl, 1-naphthyl, 2-naphthyl, 1-anthryl, 2-anthryl and 9-anthryl or the derivatives substituted once to three times by alkyl and/or halogen, preferably phenyl, 1-naphthyl and 2-naphthyl, particularly preferably phenyl.

The vicinal radicals can also be joined to form an aromatic or nonaromatic ring of from 3 to 12 carbon atoms.

The 1-hydroxyimidazoles, in particular 1-hydroxyimidazole, are valuable intermediates for synthesizing imidazole derivatives with herbicidal and antimycotic activity.

EXAMPLE 1

Preparation of 1-hydroxyimidazole hydrochloride 435 g (4 mol) of hydrogen peroxide solution (30% by weight) were added to a cooled mixture of 136 g (2 mol) of imidazole and 2240 g of 50% by weight aqueous potassium hydroxide solution. Then, at <10° C., 740 g (5 mol) of phthalic anhydride were added a little at a time, after which the mixture was stirred for 24 h.

For working up, the mixture was acidified (pH= 1.0) with sulfuric acid. The resulting precipitate was removed, and the remaining aqueous solution was made alkaline, concentrated under reduced pressure and subsequently extracted with 0.9 to 10 times the volume of butanol. The aqueous phase was reacidified and extracted with butanol. The butanol phase was concentrated, diethyl ether was added, and the solution was saturated with hydrogen chloride, when the title compound separated out and was isolated in 2.5% yield.

H-NMR (D$_2$O): 7.19, 7.22 and 8.27 (3s, 3H) [ppm]
C-NMR (D$_2$O): 118.4, 122.0 and 128.7 (3CH) [ppm]
Melting point: deliquescent

We claim:

1. A 1-hydroxyimidazole of the formula

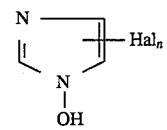

where Hal is halogen which can be identical or different and n is an integer of from 1 to 3, and the acid addition salts thereof.

2. The compound of formula Ia as claimed in claim 1 wherein Hal is selected from the group consisting of chlorine, bromine and iodine.

3. The compound of formula Ia as claimed in claim 1 wherein Hal is chlorine.

4. The compound 1-hydroxyimidazole and its acid addition salts.

* * * * *